United States Patent [19]

Matsumoto et al.

[11] Patent Number: 5,335,172
[45] Date of Patent: Aug. 2, 1994

[54] RADIATION IMAGE INFORMATION PROCESSING SYSTEM

[75] Inventors: Masayuki Matsumoto; Daigo Ezuka, both of Kanagawa, Japan

[73] Assignee: Fuji Photo Film Co., Ltd., Kanagawa, Japan

[21] Appl. No.: 755,233

[22] Filed: Sep. 5, 1991

[30] Foreign Application Priority Data

Sep. 13, 1990 [JP] Japan .................. 2-243247

[51] Int. Cl.⁵ ............................................. G06F 15/00
[52] U.S. Cl. ................................................ 364/413.13
[58] Field of Search .................. 364/413.13, 419.19

[56] References Cited

U.S. PATENT DOCUMENTS

| | | | |
|---|---|---|---|
| 4,817,050 | 3/1989 | Komatsu et al. | 364/900 |
| 4,833,625 | 5/1989 | Fisher et al. | 364/518 |
| 4,853,843 | 8/1989 | Ecklund | 364/200 |
| 4,918,588 | 4/1990 | Barrett et al. | 364/200 |
| 5,155,850 | 10/1992 | Janis et al. | 395/600 |
| 5,161,214 | 11/1992 | Addink et al. | 395/145 |
| 5,181,200 | 1/1993 | Harrison | 370/85.1 |

*Primary Examiner*—Donald E. McElheny, Jr.
*Attorney, Agent, or Firm*—Sughrue, Mion, Zinn, Macpeak & Seas

[57] ABSTRACT

Disclosed herein is a radiation image information processing system basically comprising a plurality of image reading devices, a plurality of image recording devices and CRT displays which are respectively connected to the image reading devices, and a plurality of IDTs serving as registering means to which ID information of objects and other information are inputted. Further, the radiation image information processing system is characterized in that respective ones of the registering means, which are electrically connected to one another, are electrically connected to corresponding ones of the plurality of image reading devices, and other registering means are electrically connected to the respective ones of the registering means electrically connected to the corresponding ones of the plurality of image reading devices, the respective ones of the registering means electrically connected to the corresponding ones of the plurality of image reading devices having information control functions capable of storing therein information inputted to either the respective ones of the registering means or other registering means referred to above electrically connected thereto and of reading the so-stored information therefrom as needed.

3 Claims, 8 Drawing Sheets

RADIATION IMAGE INFORMATION PROCESSING SYSTEM

BACKGROUND OF THE INVENTION

1. Field of the Invention

The present invention relates to a radiation image information processing system comprising a plurality of image reading devices each of which is used to read image information from a storage-type phosphor sheet with radiation image information of an object recorded thereon, and a plurality of registering means to each of which identification (hereinafter be abbreviated as "ID") information of an object and other information are inputted.

2. Description of the Related Art

It is known that when a certain phosphor is exposed to a radiation such as cathode rays, X-rays, α-rays, etc., the phosphor stores a part of the energy of the radiation, and when the phosphor exposed to the radiation is then exposed to stimulating rays such as a laser beam, etc., the phosphor emits accelerated or exciter light in proportion to the stored energy of the radiation. The phosphor which exhibits such a property is referred to as a "storage-type phosphor".

There has been proposed by the present applicant a radiation image information processing system employing such a phosphor, which comprises a plurality of image reading devices each of which is used to store radiation image information of an object such as a human body on a storage-type phosphor sheet and to scan such a storage-type phosphor sheet with a light beam such as a laser beam so that the storage-type phosphor sheet emits accelerated light corresponding to the radiation image information, thereby photoelectrically detecting the emitted light so as to read image information based on the result of its detection, and a plurality of registering means to each of which ID information of an object and other information are inputted (see Japanese Laid-Open Patent Publication No. 63-253348).

In the radiation image information processing system, information defining the sex, name, etc. of an object, and ID information including exposure information about the date of exposure, parts of the object to be exposed, etc. are registered before the radiation image information of the object is stored in the storage-type phosphor sheet. Therefore, there is normally provided an ID terminal (hereinafter called "IDT") serving as a registering means for the ID information in the vicinity of an exposure device. The ID information is registered in the IDT by charging the IDT with a magnetic card on which necessary information is recorded in advance or by a manual operation.

The storage-type phosphor sheet normally has a bar code serving as an identification mark used to distinguish between the storage-type phosphor sheet and each of other storage-type phosphor sheets. The IDT registers the ID information referred to above therein and reads the bar code. In addition, the IDT associates the ID information with the bar code so as to store the ID information in a storing means.

On the other hand, one of the image reading devices is charged with the storage-type phosphor sheet which has been exposed by the exposure device and reads image information and a bar code from the storage-type phosphor sheet. In this case, the bar code thus read is delivered to the storing means from which ID information corresponding to such a bar code is read. Then, the ID information is inputted to the image reading device, where the setting up of reading conditions, and image processing which are based on the ID information, are carried out. The ID information is reproduced by a reproducing device as a visible image together with the read image information.

The radiation image information processing system referred to above has a plurality of the image reading devices and a plurality of the registering means, and also includes an information control means to which the plurality of registering means and the plurality of image reading devices are connected, the information control means being capable of collectively storing therein information inputted to the plurality of registering means and suitably reading the stored information therefrom.

Thus, even a storage-type phosphor sheet in which the ID information is registered by any one of the registering means can be read by an arbitrary image reading device. In addition, a plurality of image reading devices can efficiently be operated. Since all the exposure information or the like in the whole system can be stored in the information control means, the ID information can be subjected to centralized control.

In the system of such a type that a plurality of the image reading devices and a plurality of the registering means referred to above are collectively controlled by such a single information control means, however, if the information control means is not normally operated due to trouble or the like, then the entire system cannot control the ID information, etc. When any one of a plurality of image reading devices develops trouble, such trouble exerts an influence on image processing made by other normally-operated image reading devices via the information control means.

SUMMARY OF THE INVENTION

It is therefore an object of the present invention to provide a radiation image information processing system of a type wherein each of a plurality of registering means electrically connected to a plurality of image reading devices respectively is provided so as to have an information control function without using an arrangement for centrally controlling the plurality of image reading devices and the plurality of registering means, and the transfer of information is enabled even among these registering means, thereby realizing decentralized control of ID information or the like.

It is another object of the present invention to provide a radiation image information processing system comprising a plurality of image reading devices for reading image information from storage-type phosphor sheets on which radiation image information of objects are recorded, and a plurality of registering means supplied with ID information of objects and other information, the radiation image information processing system being characterized in that respective units of the plurality of registering means are electrically connected to respectively corresponding units of the plurality of image reading devices, the plurality of registering means being electrically connected to one another, and other registering means are electrically connected to the respective units of the plurality of registering means electrically connected to the corresponding units of the plurality of image reading devices, the respective units of the plurality of registering means electrically connected to the corresponding units of the plurality of image reading devices having information control functions capable of storing therein information inputted to either the respective units of the registering means or the other registering means electrically connected thereto and of suitably reading the so-stored information therefrom.

It is a further object of the present invention to provide the radiation image information processing system wherein the respective units of the registering means electrically connected to the corresponding units of the image reading devices are electrically connected to one another through an interconnecting device for carrying out the exchange of information among these registering means.

It is a still further object of the present invention to provide the radiation image information processing system wherein either the registering means or the above other registering means have bar code readers, respectively, each of which is used to read a bar code indicative of a discrete identification number applied on a storage-type phosphor sheet.

It is a still further object of the present invention to provide the radiation image information processing system wherein either the registering means or the above other registering means have magnetic card readers, respectively, each of which is used to read ID information of an object, which is recorded on a magnetic card.

It is a still further object of the present invention to provide the radiation image information processing system wherein each of the plurality of registering means has a memory for storing therein ID information of an object and other information.

The above and other objects, features and advantages of the present invention will become apparent from the following description and the appended claims, taken in conjunction with the accompanying drawings in which a preferred embodiment of the present invention is shown by way of illustrative example.

DETAILED DESCRIPTION OF THE PREFERRED EMBODIMENTS

Figure 1:
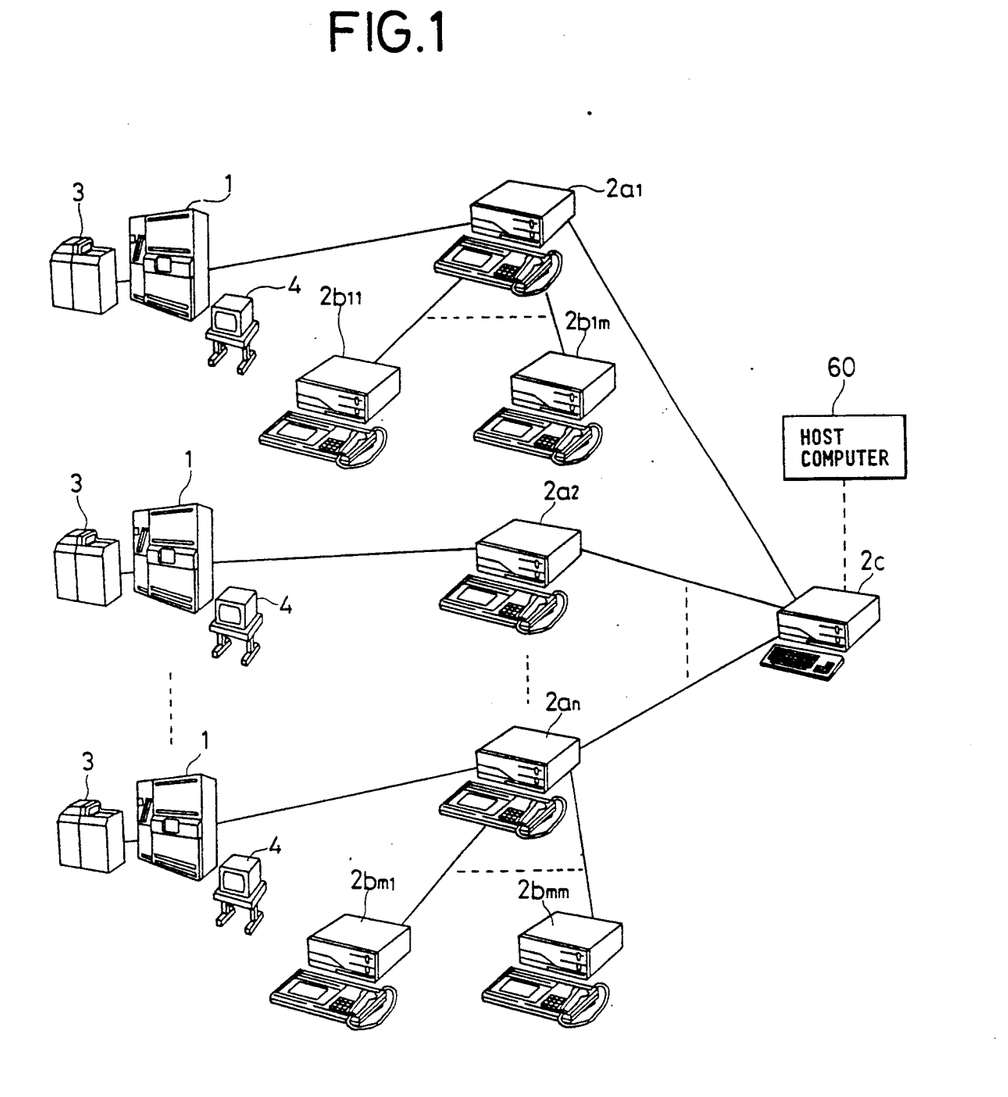
FIG. 1 is a diagram showing one example of the structure of a radiation image information processing system according to one embodiment of the present invention.

FIG. 1 is a diagram showing one example of the structure of a radiation image information processing system according to one embodiment of the present invention.

The radiation image information processing system comprises a plurality of image reading devices 1, image recording devices 3 and CRT displays 4 for confirming the image read by the image reading devices 1, which are respectively connected to the image reading devices 1, and a plurality of IDTs 2 serving as registering means to which ID information of objects and other information are inputted.

Figure 2:
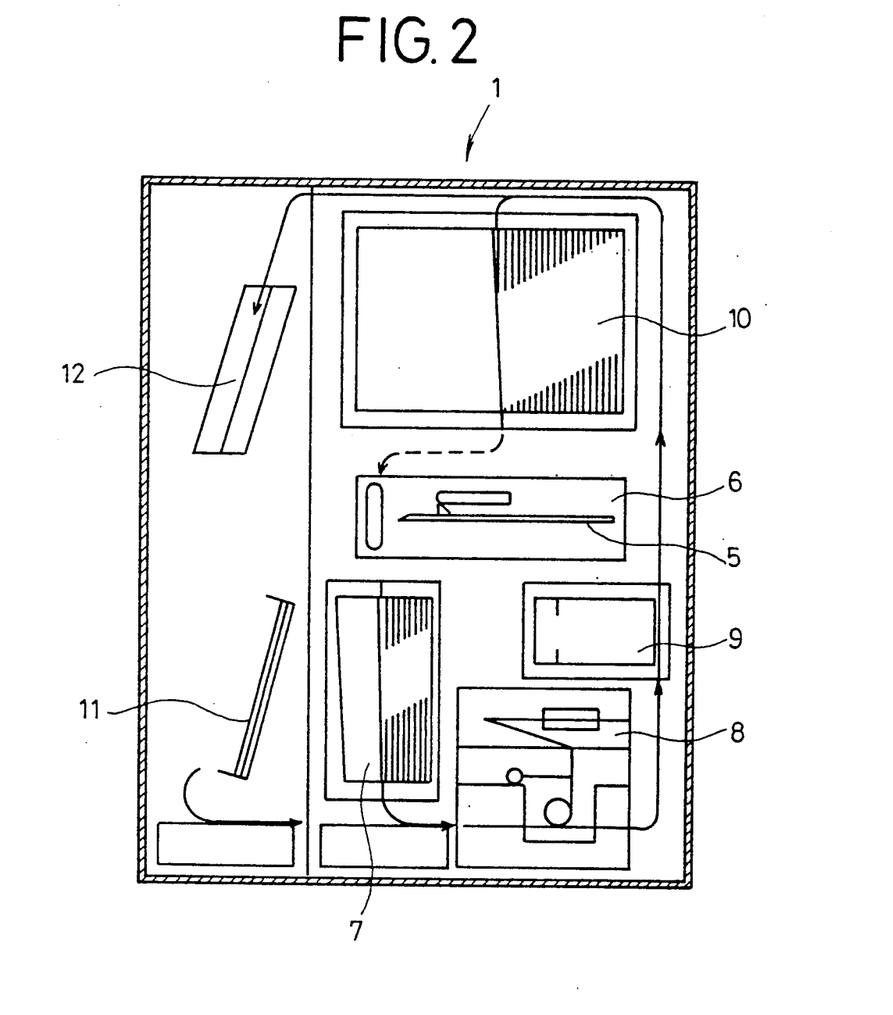
FIG. 2 is a diagram schematically showing the structure of one of image reading devices employed in the system shown in FIG. 1.

In the image reading device 1, as described above, each of storage-type phosphor sheets, on which radiation image information of an object such as a human body is stored, is scanned with a light beam such as a laser beam, so that each storage-type phosphor sheet emits accelerated light corresponding to the radiation image information. The emitted light is then photoelectrically detected so as to produce an image information signal, thereby reading image information from the image information signal. A schematic arrangement of the image reading device 1 is as follows:

As shown in FIG. 2, the image reading device 1 in the present embodiment basically comprises a cassette holding unit 6 for detachably holding cassettes 5 one by one each of which is used to accommodate the storage-type phosphor sheet therein, the cassette holding unit 6 including a mechanism for unloading sheets from the cassettes 5 held therein, a first stacker 7 capable of successively accommodating the unloaded sheets therein every predetermined sheets (e.g., 10 sheets) and of delivering the sheets accommodated therein one by one, an image reading unit 8 for scanning each sheet fed from the first stacker 7 with a laser beam so as to read image information stored on the sheet, thereby converting the same into an electric signal, an erasing unit 9 for erasing any image information which remains on each sheet thus read, and a second stacker 10 capable of successively accommodating therein the sheets from which the image information is erased and which are delivered in the upward direction by a feed means, for every predetermined sheets (for example, 30 sheets) and of supplying the sheets accommodated therein one by one to the cassette holding unit 6. With the above arrangement, any image information can be read with the present image reading device 1 by charging the cassette holding unit 6 with each cassette with the exposed storage-type phosphor sheet inserted therein from an insertion hole defined in the front of the image reading device 1.

The image reading device 1 is additionally provided with a magazine feeding unit 11 capable of accommodating therein magazines in each of which a plurality of exposed storage-type phosphor sheets are held and of unloading the respective sheets from the magazines thus held therein so as to feed the same to the image reading device 8, and a magazine dedicated tray 12 for storing therein each of the sheets unloaded from the magazines and subjected to the above image reading and erasing processes. With the above arrangement, the magazine feeding unit 11 can be charged with each of the magazines in which the plurality of exposed storage-type phosphor sheets have been stored, from an insertion slot opened at the left side as seen in front of the image reading device 1, so that the image information can be read using the image reading device 1 in a manner similar to the process of the above cassette.

Figure 3:
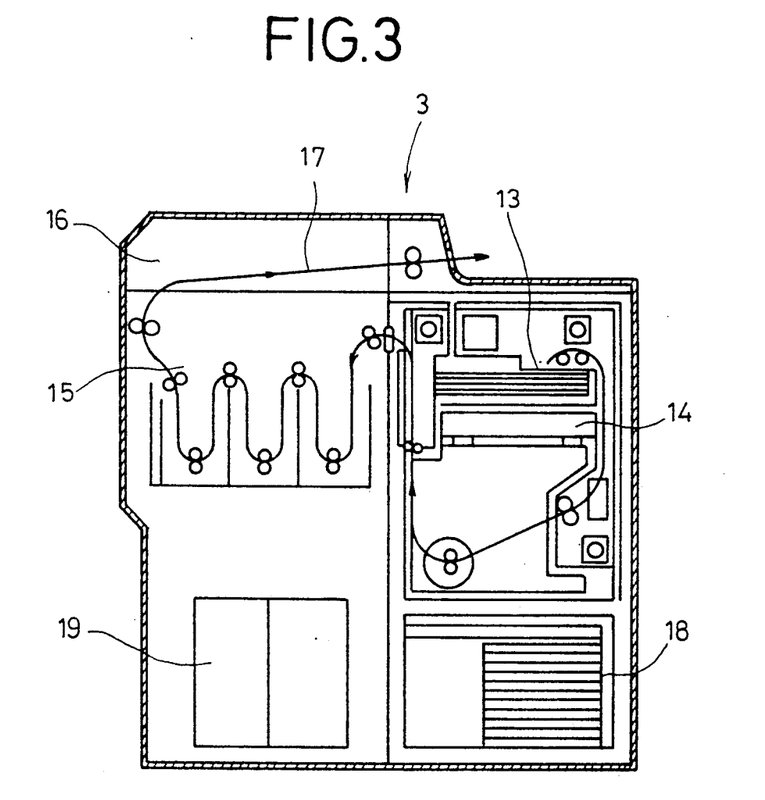
FIG. 3 is a diagram schematically illustrating the structure of one of image recording devices employed in the system shown in FIG. 1.

On the other hand, the image recording device 3 is used to record image information read by the image reading device 1 on a photographic film. A description will now be made of a schematic arrangement of the image recording device 3.

As shown in FIG. 3, the image recording device 3 comprises a charging unit 13 charged with each of photographic films, an optical processing unit 14 for receiving a signal image-processed by the image reading device 1 so as to convert the signal into a light signal to be recorded on each of the photographic films delivered from the charging unit 13, a developing processor unit 15 for developing a photographic film on which an image is recorded, a feed means 17 for passing the developed photographic film through a drying unit 16 so as to feed the same toward the upper surface of the image recording device 3, and a control unit 18 for controlling processing operations with respect to such a photographic film. In addition, the image recording device 3 also has a developer supplementing unit 19 for supplement a developer used in the developing processor unit 15.

Then, the image reading device 1 constructed as described above has one of IDTs $2a_1$ to $2a_n$, which is electrically connected thereto. An appropriate number of IDTs $2b_j$ (j = 1 to m) are electrically connected to the corresponding IDTs $2a_i$ (i = 1 to n) as needed. Further, the IDTs $2a_i$ each of which is electrically connected to the image reading device 1 are connected to one another through an IDT 2c used as an interconnecting device for carrying out the exchange of information among these IDT 2a.

A description will now be made of the IDTs 2a, 2b used as registering means and the IDT 2c used as the interconnecting device with reference to FIGS. 4 through 8.

Figure 4:
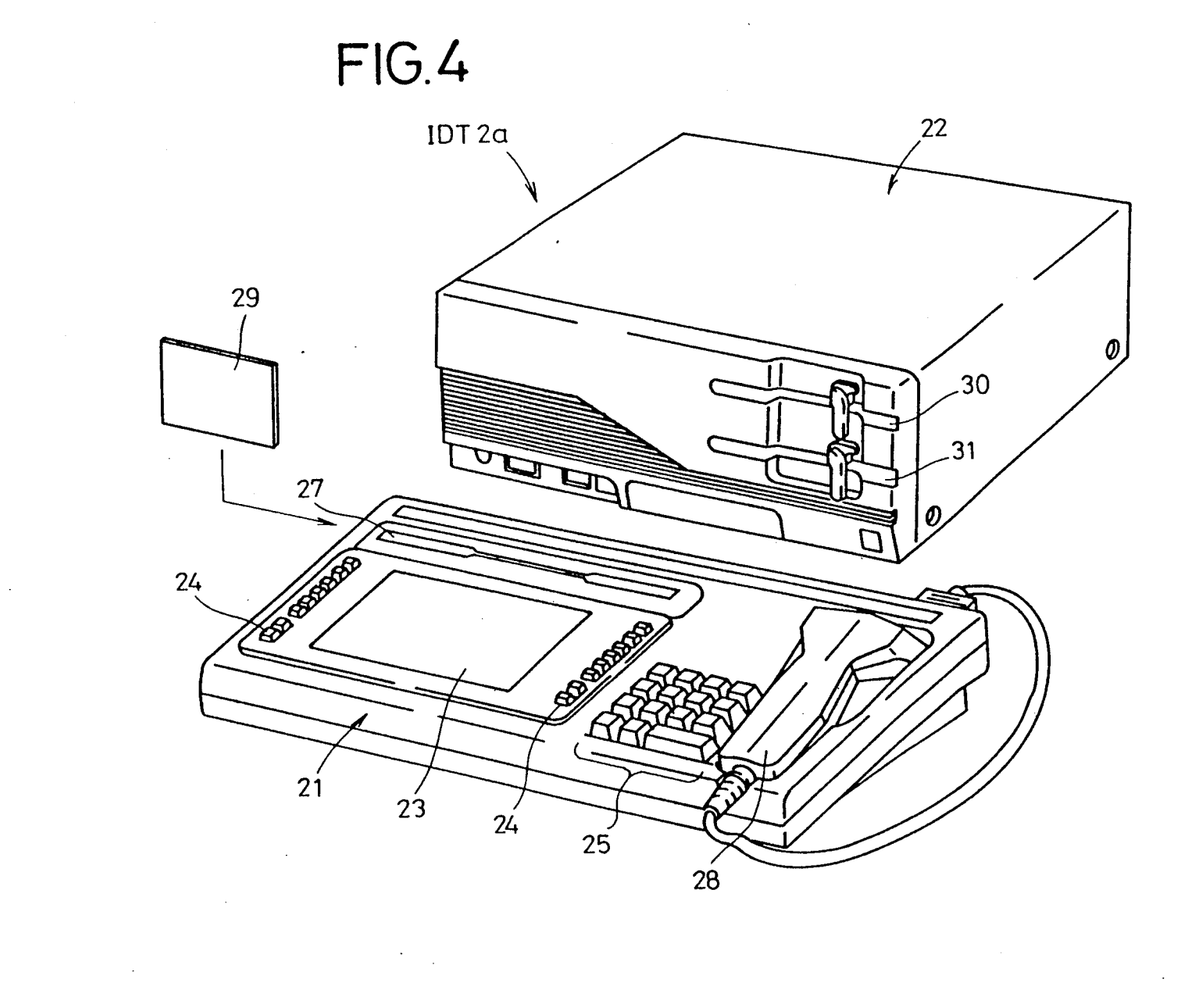
FIG. 4 is a diagram showing the appearance of one of IDTs which; electrically connected to the image reading device employed in the system.

As shown in FIG. 4, the IDT 2a, which is electrically connected to the image reading device 1, comprises an operation unit 21 and a controller 22.

The operation unit 21 has a keyboard with a rectangular display which is long in the lateral direction. In addition, there are disposed on the upper surface of the operation unit 21 a display 23 comprising liquid crystal elements or other display elements, a selection key 24 positioned on both sides of the display 23, a ten key pad 25, a slot 27 for a magnetic card reader 26 (see FIG. 5) provided inside the operation unit 21, and a bar code reader 28.

Necessary information is inputted at the time of the use of the operation unit 21 by charging the slot 27 of the card reader 26 with a magnetic card 29 with ID information or the like written therein and then reading a bar code on a storage-type phosphor sheet by the bar code reader 28. An operation picture or screen necessary for an input operation is displayed on the display 23. In addition, the ID information or the like read from the magnetic card 29 is also displayed thereon. The operator can operate the selection key 24 and the ten key pad 25 in accordance with the display of the operation screen on the display 23.

The controller 22 is shaped in the form of a rectangular parallelepiped housing, and has laterally-long slots 30, 31 defined in the front part thereof, for inserting therein a magnetic disc (not shown) used to store operation programs or the like thereon. A circuit shown in FIG. 5 is accommodated inside the housing.

Figure 5:
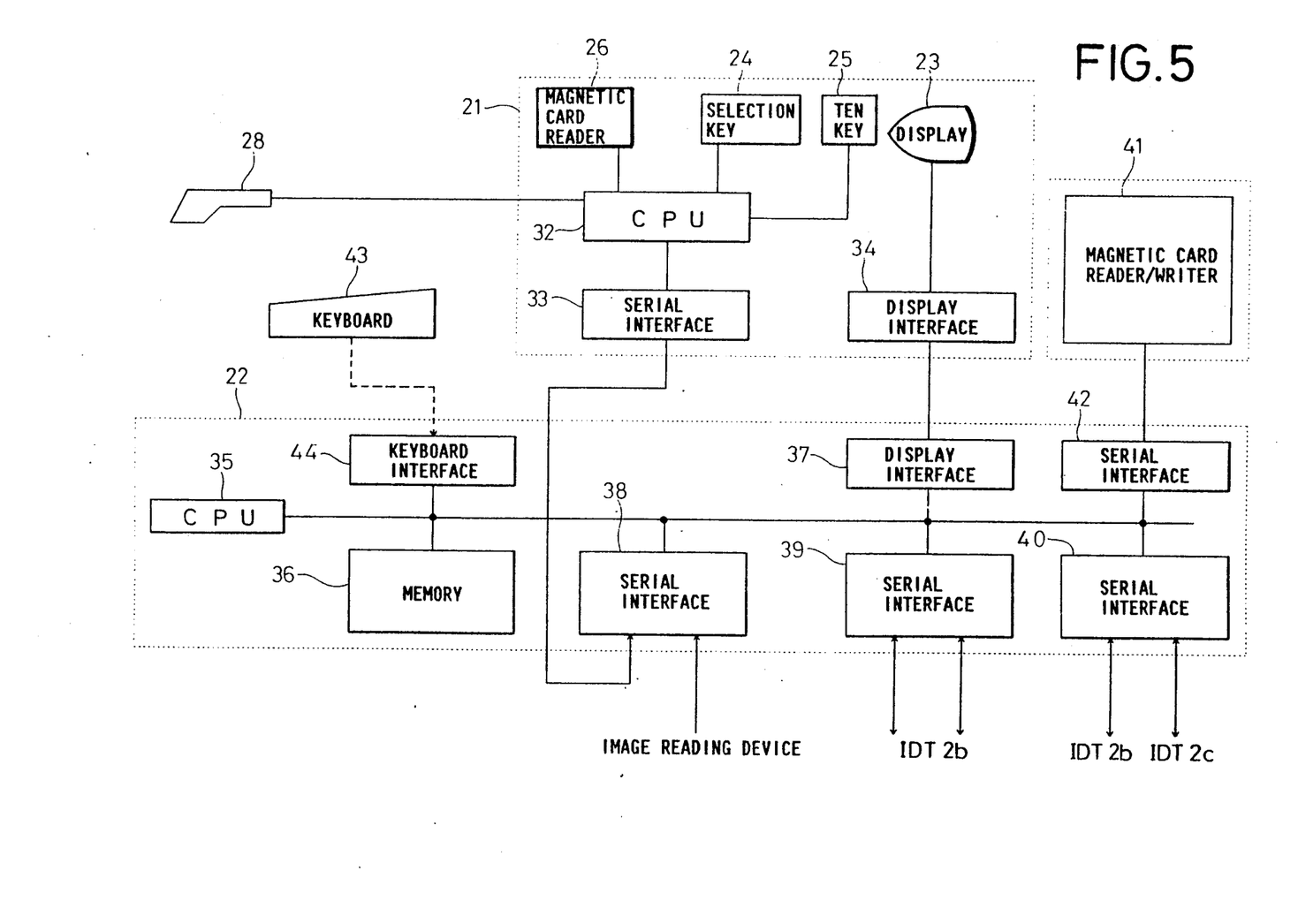
FIG. 5 is a block diagram depicting the circuit arrangement of the IDT shown in FIG. 4.

FIG. 5 shows the circuit arrangement of the IDT 2a shown in FIG. 4.

There are accommodated in the operation unit 21 a CPU 32 to which the selection key pad 24, the ten key 25, the magnetic card reader 26 and the bar code reader 28 are connected, a serial interface 33 for electrically connecting the CPU 32 to a circuit for the controller 22, and a display interface 34 for electrically connecting the display 23 to the circuit for the controller 22.

On the other hand, there are provided in the controller 22, a CPU 35, a memory 36 for storing therein information read from the magnetic disc and an ID associated with a bar code, a display interface 37 electrically connected with the display interface 34 of the operation unit 21, i.e., for providing electrical connection of the display interface 34 of the operation unit 21, a serial interface 38 electrically connected with the serial interface 33 of the operation unit 21 and with the image reading device 1, a serial interface 39 electrically connected with other IDTs 2b and a serial interface 40 electrically connected with other IDTs 2b and IDTs 2c, and a serial interface 42 electrically connected with a magnetic card reader/writer 41 as needed. Further, the controller 22 is designed so that it can be used in common even with respect to the IDT 2c serving as the interconnecting device as well as the IDT 2a used as the registering means. Therefore, the controller 22 is provided with a keyboard interface 44 for providing electrical connection of a display-free keyboard 43, in addition to the provision of the operation unit 21.

The IDT 2a stores therein information inputted thereto or information inputted to other IDT 2b connected thereto, and has an information control function for suitably taking out the stored information therefrom so as to transmit the same to the image reading device 1.

Figure 6:
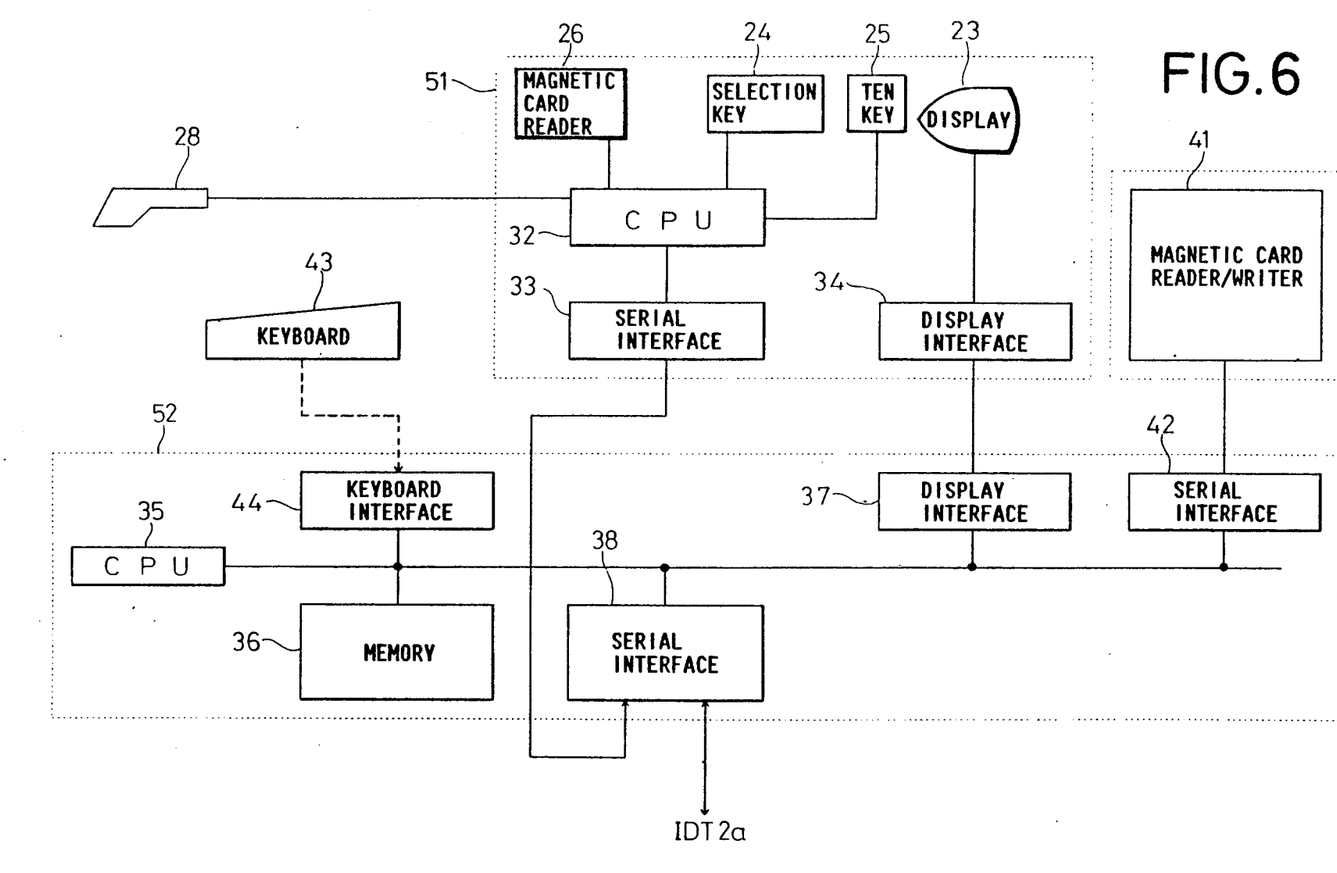
FIG. 6 is a block diagram showing the circuit arrangement of one of other IDTs, which is electrically connected to the IDT of FIG. 4.

Then, the IDT 2b, which is electrically connected to the IDT 2a, comprises an operation unit identical to the IDT 2a, and a controller in external appearance. As shown in FIG. 6, the circuit arrangement of the IDT 2b comprises an operation unit 51 identical to the operation unit 21 of the IDT 2a, and a controller 52 including only the serial interface 38, which is electrically connected with the IDT 2a in place of the image reading device 1, out of the three serial interfaces 38, 39 and 40 of the controller 22.

The IDT 2b performs only an input operation of ID information or the like and has a function for transmitting the so-input information or the like to the IDT 2a. The IDT 2b is provided for each exposure room.

Figure 7:
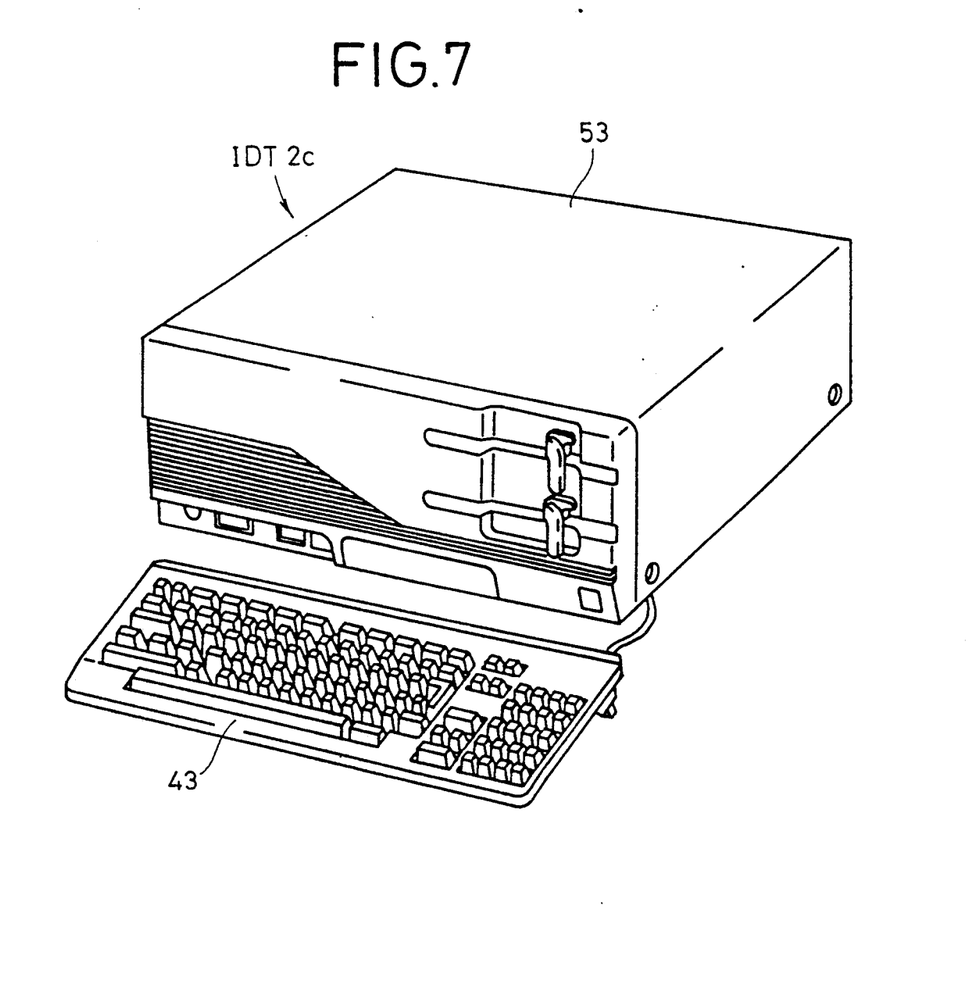
FIG. 7 is a diagram showing the appearance of an IDT connecting the individual IDTs of FIG. 4 to one another.
Figure 8:
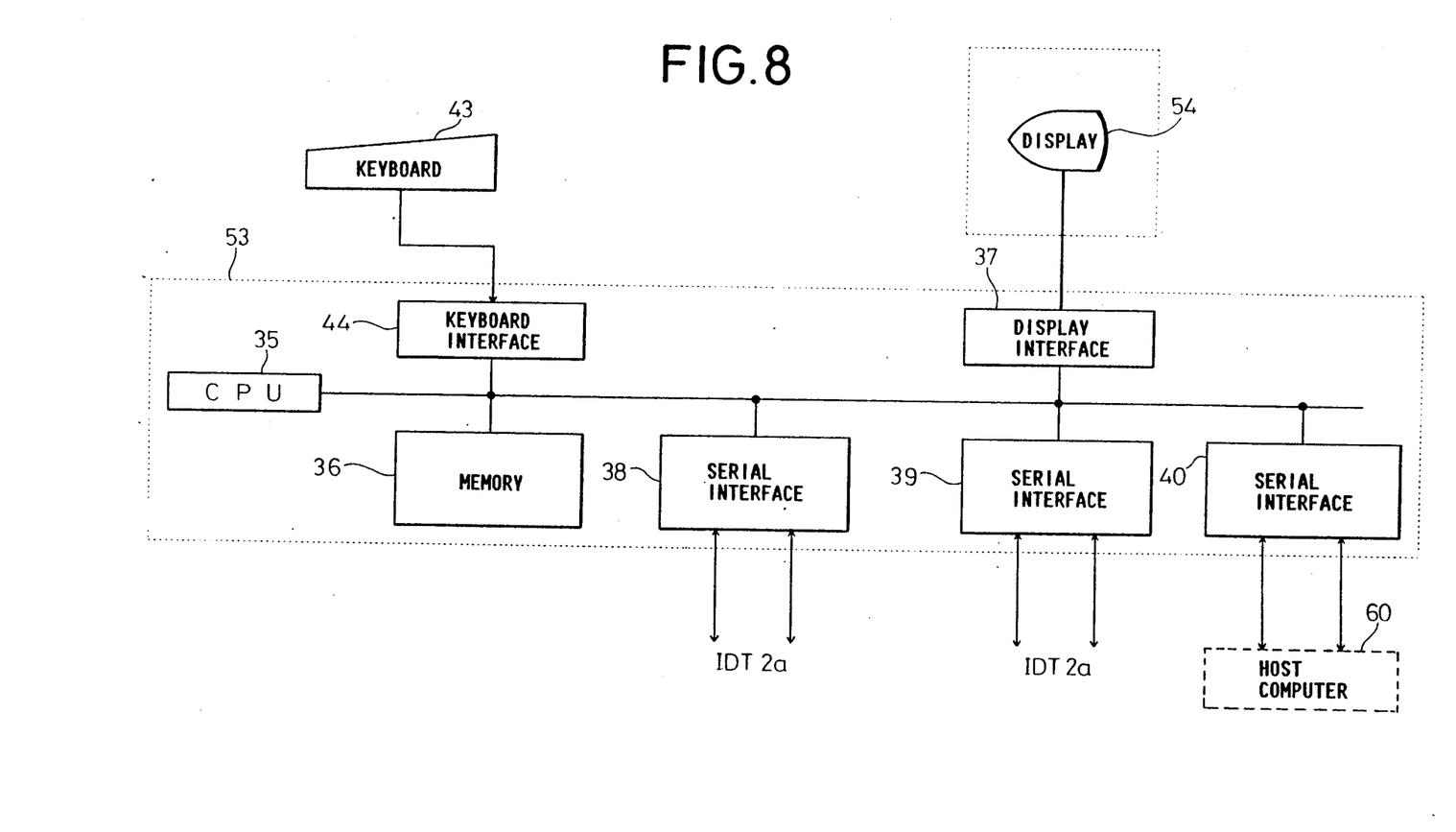
FIG. 8 a block diagram illustrating the circuit arrangement of the IDT shown in FIG. 7.

As illustrated in FIG. 7, the IDT 2c, which connects the IDTs 2a to one another, comprises a display-free keyboard 43, and a controller 53 identical to the controller of each of the IDT 2a and IDT 2b in external appearance. As depicted in FIG. 8, the circuit arrangement of the controller 53 is the same as that of the controller 22 of the IDT 2a. However, the IDT 2a is electrically connected to each of serial interfaces 38, 39 and 40. In addition, a display 54 such as a CRT, etc. is connected to a display interface 37 as needed.

The IDT 2c has a function for carrying out the exchange of ID information or the like among the IDTs 2a connected thereto. As illustrated in FIGS. 1 and 8, the IDT 2c is connected to a host computer 60, thereby enabling the transmission and control of information between the system and the host computer 60.

Operations of the present embodiment will now be described below.

When it is desired to carry out a registration process, the magnetic card 29 is first read by either the IDT 2a or the IDT 2b, and thereafter information defining the name, ID number, sex, date of birth, etc. of a patient is inputted. Then, information about parts of the patient to be exposed and an exposure method is selected from a display screen of the IDT, followed by inputting of a bar code for the storage-type phosphor sheet.

As a consequence, the bar code for the storage-type phosphor sheet, the patient information and the information about the exposed parts of the patient and the exposure method are registered in a memory 36 of the IDT 2a in such a manner that they are associated with one another. When an information input process is made by the IDT 2b, ID information is transferred to the IDT 2a at the time of the input of the bar code referred to above and then registered in the memory 36 of the IDT 2a. Incidentally, as an alternative to the use of the magnetic card, the ten key may be operated so as to input only the ID number and to input the bar code for the storage-type phosphor sheet.

The patient is photographically recorded on a storage-type phosphor sheet in accordance with the parts of the patient to be exposed and the exposure method which have been registered in the memory 36.

Then, when the image reading device 1 is charged with the storage-type phosphor sheet with the image information of the patient recorded thereon upon reading the patient information, the image reading device 1 is activated to read the bar code for the storage-type phosphor sheet and to request the IDT 2a to send the ID information corresponding to the so-read bar code. Correspondingly, the IDT 2a retrieves the patient information and the ID information such as the parts to be exposed and the exposure method, which have been registered in the memory 36, in accordance with the bar code, and then transmits the required information to the image reading device 1. When such required information is not registered in the memory 36 of the IDT 2a, the image reading device 1 transfers the bar code to the IDT 2c so as to make a request thereto for the retrieval of the patient information. Thus, the IDT 2c is activated to make a request to other IDTs 2a for the retrieval of the ID information, which exclude the IDT 2a to which the retrieval request has been made.

In doing so, other IDTs 2a determine whether or not the ID information corresponding to the bar code is registered. If it is determined to be positive, then the ID information is transferred to the IDT 2a to which the retrieval of the ID information has been made via the IDT 2c.

Thereafter, the optimum reading condition and the image processing condition are set up based on the parts to be exposed and the exposure method representative of the accessed ID information. After the reading of an image is carried out, certain image processing is made to the image thus read. Then, the so-processed image and the patient information indicative of the ID information are combined together, and the combined information is thereafter transferred to the image recording device 3, where the patient information is reproduced together with that image as a visible image.

According to the present invention, as has been described above, each of registering means respectively connected to a plurality of image reading devices is provided so as to have an information control function. In addition, the transfer of information can be made even among these registering means. Therefore, the information control can be carried out by any one of the registering means which have been connected to the image reading devices respectively, thereby enabling the distributed control of information.

Further, even when any one of a plurality of registering means or a plurality of image reading devices is out of order, the image information processing of the entire system can be achieved by using either other registering means or other image reading devices, which are normally operated.

Having now fully described the invention, it will be apparent to those skilled in the art that many changes and modifications can be made without departing from the spirit or scope of the invention as set forth herein.

What is claimed is:

1. A radiation image information processing system comprising:
    a plurality of image reading devices for reading image information from storage-type phosphor sheets on which radiation image information of objects have been recorded;
    a plurality of first registering means supplied with ID information of said objects and other information corresponding to said radiation image information recorded on said phosphor sheets, wherein each one of said image reading devices is electrically connected to a single corresponding one of said plurality of first registering means, and said plurality of first registering means being electrically connected to one another;
    a plurality of second registering means electrically connected to respective units of said plurality of first registering means;
    an interconnecting device for carrying out exchange of information among said plurality of first registering means, said respective units of said first registering means being electrically connected to one another through said interconnecting device;
    each of said first registering means further comprising memory means, wherein information is transferred between said plurality of first registering means and said plurality of second registering means such that said memory means of each of said first registering means is capable of storing therein said ID information inputted to either said first registering means or said second registering means and of reading said ID information therefrom.

2. A radiation image information processing system according to claim 1, wherein at least one of said first registering means and said second registering means comprises bar code reading means for reading a bar code indicative of a discrete identification number applied on a storage-type phosphor sheet.

3. A radiation image information processing system according to claim 1, wherein at least one of said first registering means and said second registering means comprises magnetic card reading means for reading said ID information of an object, which is recorded on a magnetic card.

* * * * *